(12) United States Patent
Kwak

(10) Patent No.: US 8,252,028 B2
(45) Date of Patent: Aug. 28, 2012

(54) POSTERIOR DYNAMIC STABILIZATION DEVICE

(75) Inventor: Seungkyu Daniel Kwak, Needham, MA (US)

(73) Assignee: DePuy Spine, Inc., Raynham, MA (US)

( * ) Notice: Subject to any disclaimer, the term of this patent is extended or adjusted under 35 U.S.C. 154(b) by 673 days.

(21) Appl. No.: 11/959,691

(22) Filed: Dec. 19, 2007

(65) Prior Publication Data
US 2009/0163954 A1    Jun. 25, 2009

(51) Int. Cl.
*A61B 17/70*    (2006.01)
(52) U.S. Cl. .................................................. 606/248
(58) Field of Classification Search .......... 606/246–279
See application file for complete search history.

(56) References Cited

U.S. PATENT DOCUMENTS

| | | |
|---|---|---|
| 4,790,303 A | 12/1988 | Steffee |
| 5,092,866 A | 3/1992 | Breard |
| 5,387,213 A | 2/1995 | Breard |
| 5,423,816 A | 6/1995 | Lin |
| 5,486,174 A | 1/1996 | Fournet-Fayard |
| 5,496,318 A | 3/1996 | Howlnd |
| 5,540,688 A | 7/1996 | Navas |
| 5,556,431 A | 9/1996 | Buttner Janz |
| 5,658,286 A | 8/1997 | Sava |
| 5,672,175 A | 9/1997 | Martin |
| 5,674,296 A | 10/1997 | Bryan |
| 5,725,582 A | 3/1998 | Bevan |
| RE36,221 E | 6/1999 | Breard |
| 6,102,912 A | 8/2000 | Cazin |
| 6,293,949 B1 | 9/2001 | Justis |
| 6,402,750 B1 | 6/2002 | Atkinson |
| 6,436,099 B1 | 8/2002 | Drewry |
| 6,595,993 B2 | 7/2003 | Donno |
| 6,761,719 B2 | 7/2004 | Justis |
| 6,783,527 B2 | 8/2004 | Drewry |
| 6,796,984 B2 | 9/2004 | Soubeiran |
| 6,835,205 B2 | 12/2004 | Atkinson |
| 6,966,910 B2 | 11/2005 | Ritland |
| 6,986,771 B2 | 1/2006 | Paul |
| 6,989,011 B2 | 1/2006 | Paul |
| 7,018,379 B2 | 3/2006 | Drewry |
| 7,029,475 B2 | 4/2006 | Panjabi |
| 7,125,410 B2 | 10/2006 | Freudiger |
| 7,326,210 B2 | 2/2008 | Jahng |
| 7,329,258 B2 | 2/2008 | Studer |
| 7,559,942 B2 | 7/2009 | Paul |
| 7,604,653 B2 | 10/2009 | Kitchen |
| 7,625,393 B2 | 12/2009 | Fallin |

(Continued)

FOREIGN PATENT DOCUMENTS

EP    677277    10/1995

(Continued)

OTHER PUBLICATIONS

Hefti, "Repair of lumbar spondylolysis with a hook-screw", Int Orthop 1992, pp. 81-825, vol. 16(1)—abstract.

*Primary Examiner* — Eduardo C Robert
*Assistant Examiner* — Summer Kostelnik

(57) ABSTRACT

A posterior dynamic stabilization system that allows a) elongation through a ligament connected to the bone anchors that ultimately reaches its full length to provide a secure flexion limit, and b) compression through a spacer positioned between bone anchors to provide an extension limit.

15 Claims, 6 Drawing Sheets

U.S. PATENT DOCUMENTS

| | | |
|---|---|---|
| 2003/0088251 A1* | 5/2003 | Braun et al. .................. 606/73 |
| 2003/0109880 A1 | 6/2003 | Shirado |
| 2003/0220643 A1* | 11/2003 | Ferree ............................ 606/61 |
| 2004/0002708 A1 | 1/2004 | Ritland |
| 2004/0049189 A1 | 3/2004 | Le Couedic |
| 2004/0049190 A1 | 3/2004 | Biedermann |
| 2004/0073215 A1 | 4/2004 | Carli |
| 2004/0215192 A1 | 10/2004 | Justis |
| 2004/0225289 A1 | 11/2004 | Biedermann |
| 2004/0267260 A1 | 12/2004 | Mack |
| 2005/0049708 A1 | 3/2005 | Atkinson |
| 2005/0056979 A1 | 3/2005 | Studer |
| 2005/0065514 A1 | 3/2005 | Studer |
| 2005/0065516 A1 | 3/2005 | Jahng |
| 2005/0085814 A1 | 4/2005 | Sherman |
| 2005/0085815 A1 | 4/2005 | Harms |
| 2005/0113927 A1 | 5/2005 | Malek |
| 2005/0124991 A1 | 6/2005 | Jahng |
| 2005/0149020 A1 | 7/2005 | Jahng |
| 2005/0177157 A1 | 8/2005 | Jahng |
| 2005/0203513 A1 | 9/2005 | Jahng |
| 2005/0203514 A1 | 9/2005 | Jahng |
| 2005/0267470 A1* | 12/2005 | McBride ....................... 606/61 |
| 2006/0036240 A1 | 2/2006 | Colleran |
| 2006/0036325 A1 | 2/2006 | Pul |
| 2006/0064090 A1 | 3/2006 | Park |
| 2006/0084991 A1 | 4/2006 | Borgstrom |
| 2006/0142758 A1 | 6/2006 | Petit |
| 2006/0142760 A1 | 6/2006 | McDonnell |
| 2006/0189983 A1 | 8/2006 | Fallin |
| 2006/0195093 A1 | 8/2006 | Jahng |
| 2006/0212033 A1 | 9/2006 | Rothman |
| 2006/0247637 A1 | 11/2006 | Colleran |
| 2007/0005063 A1 | 1/2007 | Bruneau |
| 2007/0016190 A1 | 1/2007 | Martinez |
| 2007/0016201 A1 | 1/2007 | Freudiger |
| 2007/0055244 A1 | 3/2007 | Jackson |
| 2007/0118119 A1 | 5/2007 | Hestd |
| 2007/0123871 A1 | 5/2007 | Jahng |
| 2007/0213821 A1 | 9/2007 | Kwak |
| 2007/0225710 A1 | 9/2007 | Jahng |
| 2007/0233075 A1 | 10/2007 | Dwson |
| 2007/0276380 A1 | 11/2007 | Jahng |
| 2008/0033435 A1 | 2/2008 | Studer |

FOREIGN PATENT DOCUMENTS

| | | |
|---|---|---|
| EP | 669109 | 5/1999 |
| EP | 1388323 | 1/2007 |
| GB | 269753 | 2/1994 |
| WO | WO 9641582 | 12/1996 |
| WO | WO 0145576 | 6/2001 |
| WO | WO 0156489 | 8/2001 |
| WO | WO 0207622 | 1/2002 |
| WO | WO 02102259 | 12/2002 |
| WO | WO 03047441 | 6/2003 |
| WO | WO 2005094704 | 10/2005 |

* cited by examiner

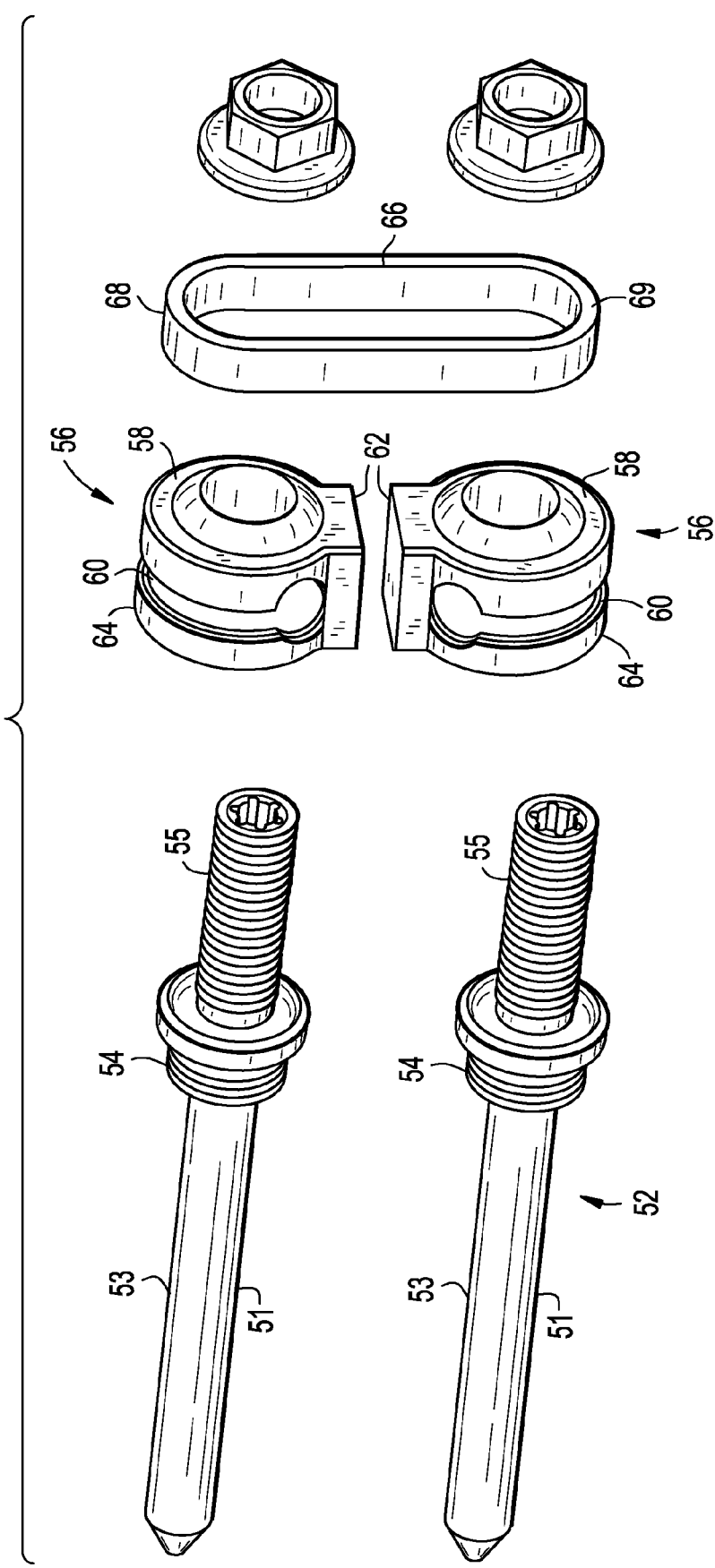

POSTERIOR DYNAMIC STABILIZATION DEVICE

BACKGROUND OF THE INVENTION

Most of the currently available posterior dynamic stabilization (PDS) devices accommodate bending of the rod. However, if a functional spinal unit (FSU) rotates about a point away from the rod, the rod should elongate and/or compress in addition to bend. Furthermore, a PDS device may limit the motion of an FSU by providing a limit to flexion (i.e., elongation of PDS) or extension (i.e., compression of PDS).

A normal functional spine unit (i.e., two adjacent vertebral segment with a disc in between) has a center of rotation generally near the center of the disc or at least around the vertebral body column. Therefore, any PDS device that is attached to pedicle screws must not only bend but also elongate and compress to allow motion in an FSU.

Furthermore, the need for a PDS device that can elongate and compress becomes more important when a disc replacement prosthetic is implanted, since most disc replacement prosthetics are ball and socket type joints that define the center of vertebral rotation to be near the center of disc. With the center of rotation forced to be in the anterior portion by the disc replacement, the PDS device must elongate and compress to allow vertebral motion.

U.S. Pat. No. 4,790,303 (Steffee) discloses a fastener for securing bone graft between a pair of bone portions. The fastener includes a curved elongated member having a shank for extending into the bone graft and pair of bone portions. The shank has an end portion which receives a force for driving the shank into the pair of bone portions and the bone graft. The shank has a plurality barbs projecting therefrom for resisting movement of the shank relative to the bone graft and the bone portions.

U.S. Pat. No. 5,092,866 (Breard I) discloses an inter-vertebral stabilizer having one or more flexible ligaments. Each flexible ligament can be engaged with two respective vertebrae and/or associated with two retaining elements, such as screws, each of which is suitable for being implanted in a respective vertebra. The present invention also relates to a process, and the associated apparatus, for determining or verifying the tension of such an inter-vertebral stabilizer before it is put into place on the spinal column. This process includes implanting, in each of the vertebrae concerned, a corresponding rigid rod extending outside the patient's body. The rods in each pair of adjacent rods are immobilized in an initial position. If the pain which is to be removed by the stabilizer persists, the process includes modifying the distance between the rods, then in immobilizing the rods in their new relative positions and in repeating the pain test. This cycle of operations is repeated, if necessary, until the pain disappears. The length to be allocated to the ligament is deduced from the distance then attained between the two rods.

U.S. Pat. No. 5,387,213 (Breard II) discloses a surgical implant for connecting two flexible ligaments to vertebrae having an intervertebral stabilizer including an intra-osseous rod having a first end for implanting into a vertebra. The intervertebral stabilizer also includes an extra-osseous head extending outwardly of the vertebrae. The extra-osseous head has two stepped portions, each with a peripheral surface, defining two ligament retaining zones. Each of the two ligament retaining zones has a shoulder, forming an axial ligament abutment on the sides of the ligament retaining zones closest to the first end. The extra-osseous head retains two flexible ligaments spaced from the vertebrae and each other by the shoulders.

U.S. Pat. No. 5,725,582 (Bevan) discloses a surgical implant comprises a hank formed from a single strand of flexible biocompatible material (such as polyester) with at least one bight at each end of the hank and a tail extending from one end, and a crimpable sleeve-like element encircling the overlapping end lengths of the strand. The implant is shown in use for the stabilization of the spine, the bights being applied to hooking members engaged respectively with the lamina of one vertebra and the spinous process of an adjacent vertebra, the strand material being tensioned by pulling the tail before crimping the sleeve-like element.

U.S. Pat. No. 6,436,099 (Drewry I) discloses an apparatus provided to allow for an adjustable length tether for use in the spine and other parts of the body. The tether comprises an artificial strand with an eyelet formed in one end, the other end being looped through the eyelet. The other end is then secured with respect to the eyelet by a crimp, the excess length being cut off after the length of the tether has been given an appropriate tension. Alternatively, the eyelet end may be formed around a grommet. The crimp may be separate from the grommet or a part of the grommet. The mechanism by which the length is adjusted in some cases will take advantage of the shape memory properties of alloys such as nickel-titanium.

WO 2001-45576 (Mulholland) discloses an assembly used for the stabilisation of two adjacent vertebral bodies of the spine. It comprises two pedicle screws, having a threaded shaft with a tapering first end for introduction into the vertebral bodies and a head portion with a second end. It further comprises a flexible longitudinal fulcrum with two portions, which can be disposed transversely to said pedicle screws, and fixed with its end portions to the head portions of said two pedicle screws at a distance x from said second end. The assembly further comprises an elastic ligament which can be disposed transversely to said two pedicle screws and fixed to the head portions of said two pedicle screws at a distance y<x from the end portion of the fulcrum. By introduction of a fulcrum, lying close to the axis of flexion and extension of the spinal motion segment, the posteriorly placed ligament distracts the whole disc, and the fulcrum itself becomes a load-bearing structure. This reduces the load over the disc, and makes it an even distribution of load across the end-plate throughout the range of movement of the motion segment, that is allowed by the implant.

U.S. Pat. No. 6,783,527 (Drewry II) discloses devices, methods and systems for stabilizing at least a portion of the spinal column. Devices include anchors and coupling members for engaging an elongate member. Systems include an elongate member sized to span a distance between at least two vertebral bodies and being at least partially formed of a flexible material. A number of anchors and coupling members are used to secure the elongate member to each of the vertebral bodies. The anchors can be compressed towards one another and the elongate member secured thereto and/or the elongate member can be tensioned to provide corrective forces to the spine.

U.S. Pat. No. 7,018,379 (Drewry III) discloses Devices, methods and systems for stabilizing at least a portion of the spinal column are provided. Devices include anchors and coupling members for engaging an elongate member. Systems include an elongate member sized to span a distance between at least two vertebral bodies and being at least partially formed of a flexible material. A number of anchors and coupling members are used to secure the elongate member to each of the vertebral bodies. The anchors can be compressed towards one another and the elongate member secured thereto and/or the elongate member can be tensioned to provide corrective forces to the spine.

EP Patent No. 0669109 (Dubois) discloses a system to stabilize adjacent vertebrae having a pressure-resistant support body to transfer pressure forces between two screw heads. The strip is of an elastic plastics material with a round cross section to withstand shear forces, fitting into matching drillings to be held on all sides at the support and screw head and to center the support and screw head with each other. The strip is pretensioned to hold the support and screw head together at a support surface round the strip. The elastic material for the support is preferably polyurethane.

SUMMARY OF THE INVENTION

In accordance with the present invention, there is provided a posterior dynamic stabilization system, comprising:
- a) first and second bone anchors having a distal end having a threadform and a proximal end,
- b) a first flexible belt ligament having a first end portion and a second end portion, and
- c) a spacer having a first end and a second end, the spacer being disposed between the respective bone anchors, wherein each end portion of the flexible belt ligament is attached to a respective bone anchor, and
wherein the spacer is positioned between the two bone anchors to contact each bone anchor during spinal extension.

The present invention is posterior dynamic stabilization (PDS) device that allows predetermined a) elongation through a ligament connected to the bone anchors that ultimately reaches its full length to provide a secure flexion limit, and b) compression through a spacer positioned between bone anchors to provide an extension limit.

In flexion of the spine, the belt (ligament) limits the motion. Hence, in a normal setting, the ligament is lax or loose and only becomes tight at the flexion limit. On the other hand, the spacer is rigid or semi-rigid to stop extension of the spine. In a normal or neutral setting, the spacer does not contact either or both of the superior and inferior pedicle screws.

DESCRIPTION OF THE FIGURES

FIG. 5*a* discloses an exploded view of the spacerless device of the present invention.

DETAILED DESCRIPTION OF THE INVENTION

Figure 1:
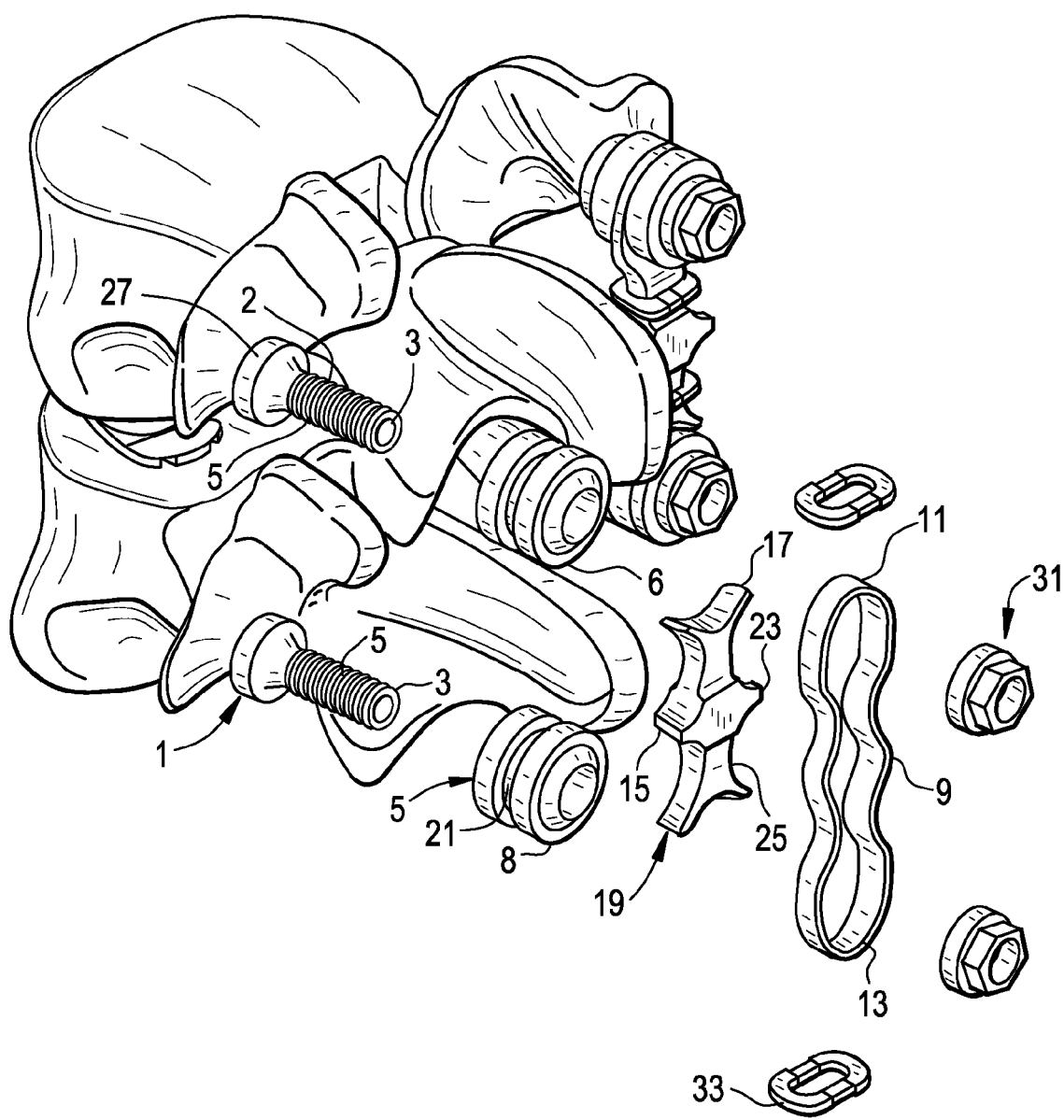
FIG. 1 is an exploded version of a first embodiment of the present invention.

Now referring to FIG. 1 there is provided a posterior dynamic stabilization system, comprising:

- a) first 1 and second 2 bone anchors having a distal end having a first threadform (not shown) and a proximal end 3 having a second threadform 5,
- b) first and second belt retainers 5 having a third threadform (not shown) that mates with the second threadform an inner portion 6 and an outer portion 8,
- c) a first flexible belt ligament 9 having a first end portion 11 and a second end portion 13, and
- d) a spacer 15 having a first end 17 and a second end 19, each end disposed within the inner portion of the channel of the respective bone anchor, wherein the belt retainers are locked onto the second threadform of each bone anchor,
wherein each end portion of the flexible belt ligament is attached to a respective belt retainer, and
wherein the spacer is positioned between the two belt retainers to contact each belt retainer during spinal extension and be free of each belt retainer during spinal flexion.

The flexible belt ligament serves as an ultimate flexion stop of the functional spinal unit. As a belt, it should bend at least in one direction easily. At the point of maximum allowed flexion, the belt straightens, thereby preventing further separation of the bone anchors and limiting flexion. In a normal setting, the belt does not perform its limiting function, but rather folds in various ways guided by other mechanical components of the PDS device (such as the extension spacer and side springs). The belt can be made of any flexible material including woven fibers (both natural and synthetic), thin metallic band, or polymeric band.

For the purposes of the present invention, when it is stated that each end portion of the flexible belt ligament is attached to a respective bone anchor, such attachment may include either direct attachment or indirect attachment through a belt retainer.

In some embodiments, the belt ligament can be a single strap that connects superior and inferior pedicle screws. In these strap embodiments, the first portion of the belt comprises a first end, and the second portion of the belt comprises a second end. Each end of this strap belt attaches to a respective bone anchor, preferably the retainer portion of the bone anchor, to provide a simple single strap-like component that resists excessive flexion and elongation.

In some embodiments, the device further comprises d) a second flexible belt ligament having a first end portion and a second end portion, each end portion contacting the respective bone anchor. Each end of both of these belts is a strap that attaches to each respective bone anchor, preferably the retainer portion of the bone anchor, to provide a dual component system that resists excessive flexion and elongation. The dual ligament nature of this embodiment provides redundancy and load sharing in its resistance to excessive flexion and elongation In some embodiments, the first and second ligaments comprise a single continuous belt. In this embodiment, the retainer preferably has a tranverse channel 21 present on its side facing away from the other retainer (i.e., the first retainer's outer portion), so that a first portion of the belt can fit in that transverse channel and a second portion of the belt can fit in a second channel similarly present on the outer portion of the second retainer. Each retainer preferably has a continuous channel extending around the periphery of the retainer so that the continuous belt can fit into a portion of the channel irrespective of the final position of the tightened retainer. The continuous belt embodiment has the same load sharing and redundancy advantages provided by the dual strap embodiment, but further has the advantage of having a low stress attachment to the corresponding retainers. This low stress attachment is accomplished by having a high surface area contact between the belt retainers and the continuous belt.

The extension spacer serves as an ultimate extension limit. In maximum allowed extension, it contacts superior and inferior pedicle screws (or other attachment to the screws such as a belt channel). In other embodiments, the spacer can be a hollow box where the ligament is located inside the box. In the extreme case where the space between the pedicle screws is limited (e.g., L5-S1 level), the extension spacer can be built into a pedicle screw to limit the motion. The extension spacer can be made of rigid or semi-rigid material such as metal, ceramic, plastic or semi-rigid polymers such as polyurethane, silicone, PEEK or CFRP.

The spacer generally has a longitudinal length that is slightly less than the distance between belt retainers. In this condition, the spacer has no function in a neutral setting, but acts as a stop during extreme extension, when the two retainers move towards each other. In some preferred embodiments, the spacer has a first end and a second end, wherein the first end contacts the first retainer and the second end contacts the second retainer during extreme extension. Preferably, each end of the spacer has a shape corresponding to the shape of the retainer it contacts. More preferably, each end of the spacer has a concave shape corresponding to the convex shape of the retainer it contacts. Most preferably, the shape of each end of the spacer is a concave portion of a circle corresponding to the convex circular shape of the retainer it contacts.

In some embodiments, the spacer generally has a transverse width that is slightly less than the diameter of belt retainers. In this condition, the side surfaces 23 of the spacer that define the width does not interfere with the extension of the continuous belt around the two retainers. In some embodiments, these two side surfaces are parallel to each other and flat. In other preferred embodiments, the two side surfaces have concave recesses 25 therein. These apexes of these recesses form positive stops for the contraction of the side springs. In more preferred embodiments, the two side surfaces each have a pair of concave recesses 25 therein.

The bone anchor can take the form of any typical bone anchor commonly used in the spinal fixation art. Typically, the bone anchor takes the form of a screw, more typically a pedicle screw having a distal end having a threadform, an intermediate portion having a transverse ledge 27, and a proximal end having a post which may form a second threadform.

Generally, the distal end of the screw is threaded so as to anchor the bone anchor within the vertebra. The first threadedform can take the form of any threadedform commonly used in the spinal fixation art for fixing the anchor within bone.

The ledge that separates the two threadforms generally has the functions of limiting penetration of the screw into the bone.

Generally, the proximal end of the screw is threaded so as to allow fixation of belt retainer thereto. The second threadedform can take the form of any threadform commonly used in the spinal fixation art for fixing a nut to the anchor.

In some embodiments, a belt retainer such as a locking nut is fitted over the proximal end of each anchor. The belt retainer comprises an annulus having a circumferential channel 21 therein, an inner portion and an outer portion. The circumferential channel 21 is also referred to as a "belt channel". The belt channel serves as guide for attaching the belt ligament to the bone anchor, so that the belt ligament sits in the belt channel. Moreover, the spherical front and back surfaces allow for polyaxial alignment of the belt retainer with the bone anchor, which can then be locked with a locking nut. Furthermore, the bottom indentation serves as location to contact the extension spacer.

The belt retainer may be considered to be a part of the bone anchor. In some embodiments, the distal portion of the belt retainer has a hemispheric shape so that it can mate with a corresponding hemispheric shape on the proximal portion of the bone anchor ledge, so that together the bone anchor and belt retainer form a polyaxial screw. As such the bone anchor and belt retainer combination may be considered to form a polyaxial screw. Thus, when it is stated that each end portion of the flexible belt ligament is attached to a respective bone anchor, such attachment may include either direct attachment or indirect attachment through a belt retainer.

In some embodiments, each end of the belt ligament is disposed within an outer portion of the channel.

Typically, a conventional locking nut 31 is used to lock the assembly together. This locking nut is threaded onto the proximal portion of the bone anchor after the belt retainer has been threaded onto the proximal portion of the bone anchor.

In some embodiments, the device further comprises d) first and second side springs 33, wherein the first side spring wraps around the first portion of the belt, and the second side spring wraps around the second portion of the belt. The flexible side springs hold the belt ligament and the spacer together. It prevents the spacer from coming out of the device, and holds the belt to hug the spacer. Moreover, the side spring generates a small tensile force as the belt ligament straightens. Therefore, in the neutral zone near normal motion, small tensile force guides the motion. Near the ultimate flexion limit, the stiffness of the side springs increases to limit the motion.

Figure 2A:
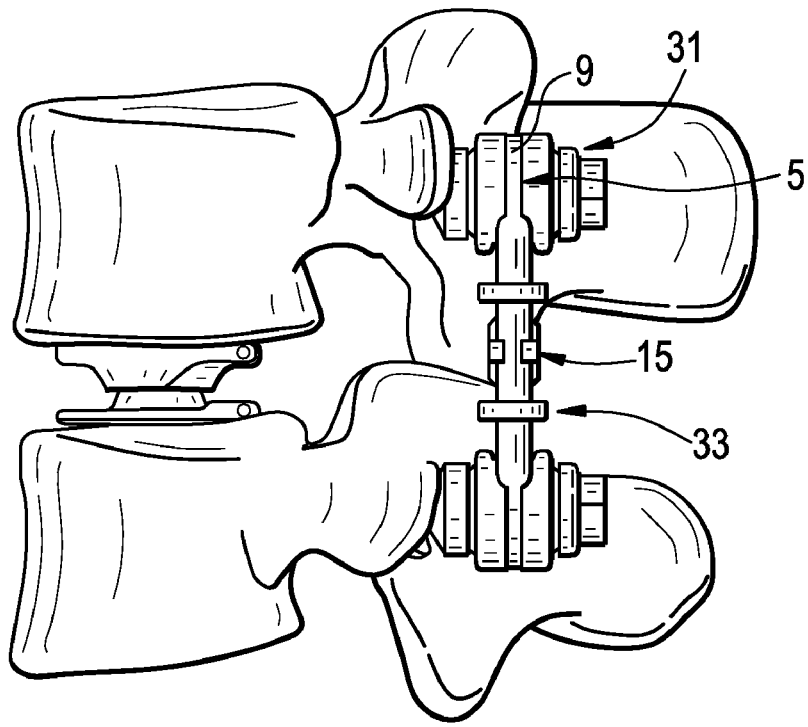
FIGS. 2*a* and 2*b* are respective side and posterior views of the device of the present invention implanted in a functional spinal unit that is subject to spinal extension.
Figure 2B:
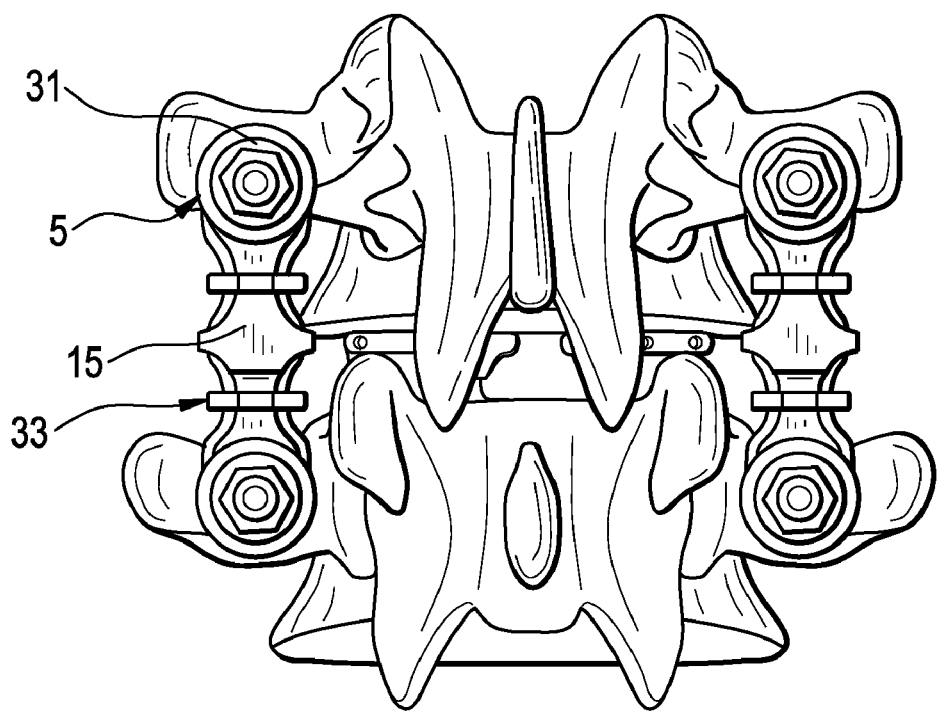

Now referring to FIGS. 2a and 2b, there is provided respective side and posterior views of the device of the present invention implanted in a functional spinal unit that is subject to spinal extension. During spinal extension, the two bone anchors move closer together as do the two belt retainers 5, thereby imparting a compressive force on the device. In this condition, the spacer 15 acts as the ultimate limiting feature of the spinal extension, as its opposite ends come into contact with the inner portions of the respective belt retainers. The belt ligament 9 is in a lax condition, and it conforms to the shape of the spacer side walls due to the tensile forces produced by the side springs 33.

Figure 3A:
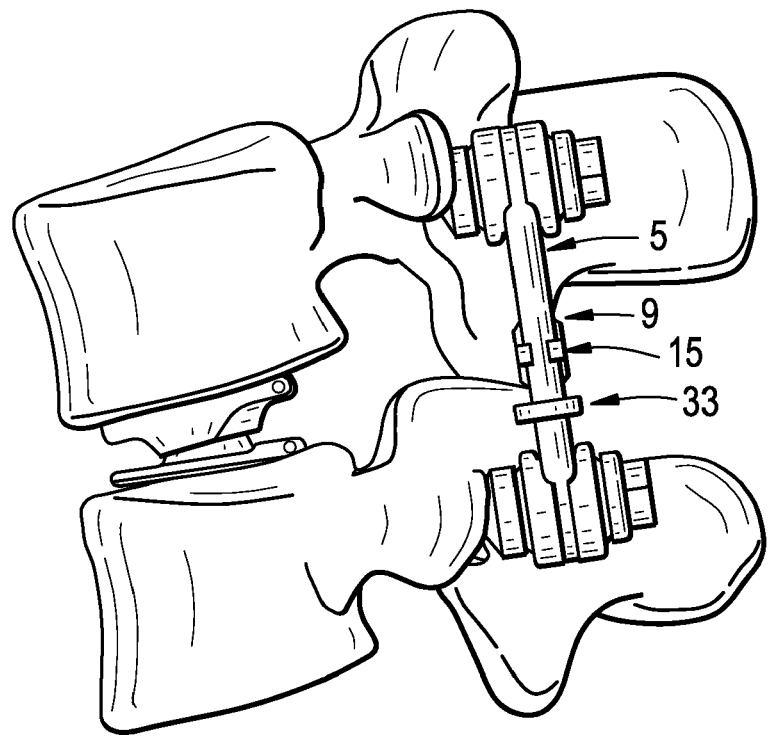
FIGS. 3*a* and 3*b* are respective side and posterior views of the device of the present invention implanted in a functional spinal unit that is subject to spinal flexion.
Figure 3B:
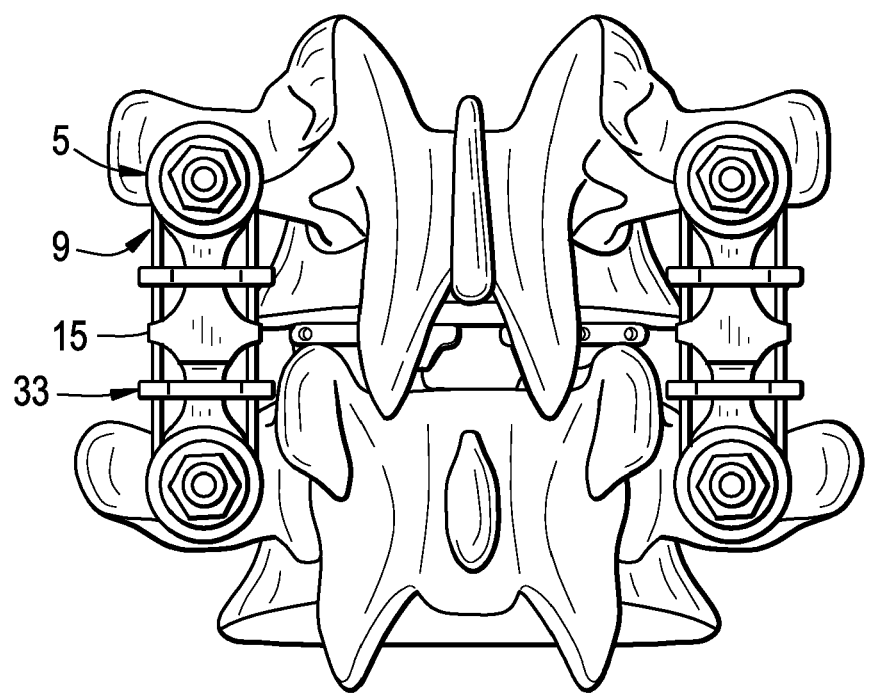

Now referring to FIGS. 3a and 3b, there is provided respective side and posterior views of the device of the present invention implanted in a functional spinal unit that is subject to spinal flexion. During spinal flexion, the two bone anchors move farther apart (as do the two belt retainers 5), thereby imparting a tensile force on the ligament 9. In this condition, the belt ligament acts as the ultimate limiting feature of the spinal flexion, as it is stretched to its ultimate length. The belt ligament is in a taut condition, and its tautness produces a tensile force on the side springs 33, which open in response to this tensile force. Also in this condition, the spacer 15 does not contact the belt retainers.

In some embodiments, the PDS device of the present invention is used with an intervertebral disc replacement (motion disc).

Figure 4:
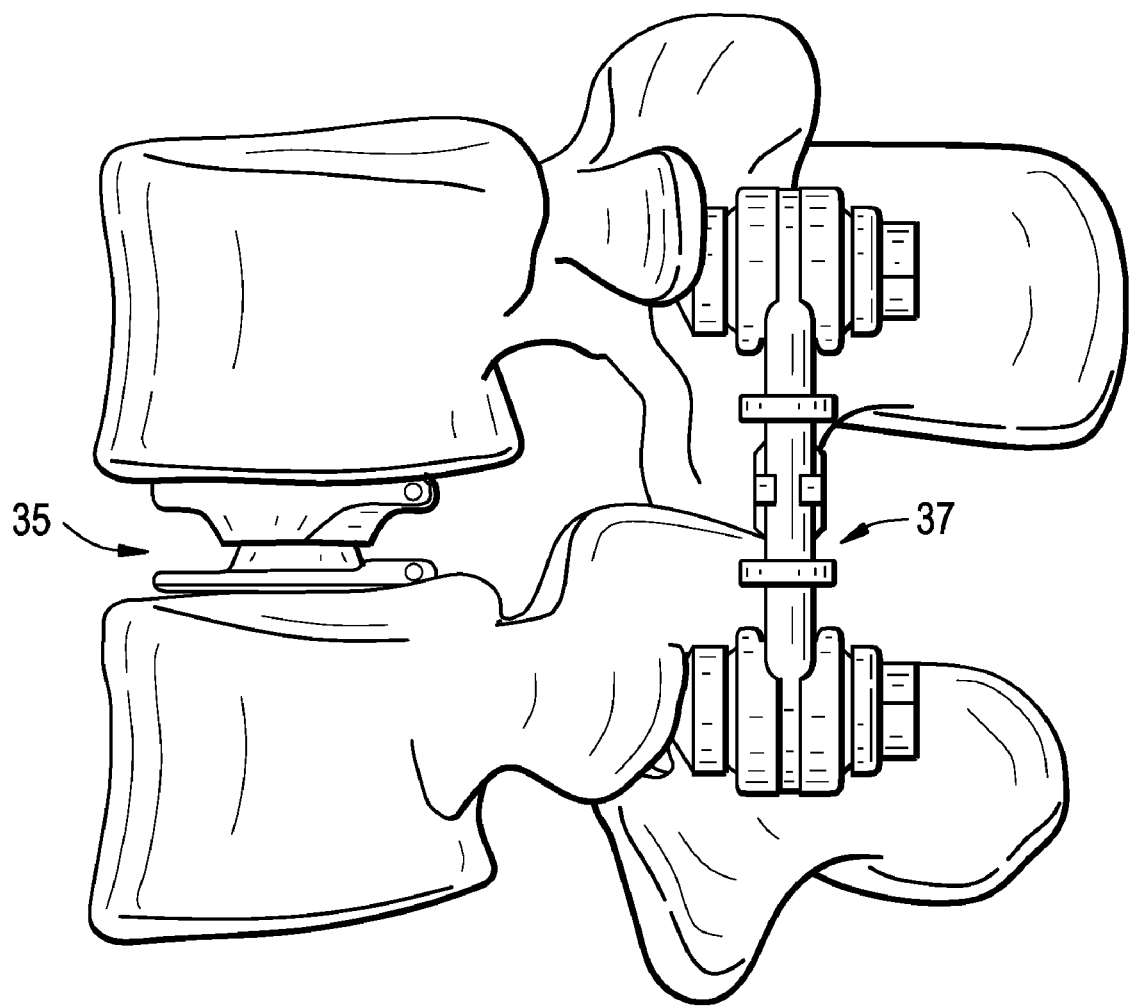
FIG. 4 discloses a side view of a functional spinal unit having both a PDS device of the present invention implanted on the posterior side of the spinal cord and a motion disc implanted within the disc space anterior to the spinal cord.

FIG. 4 discloses a side view of a functional spinal unit having both a PDS device 37 of the present invention implanted on the posterior side of the spinal cord and a motion disc 35 implanted within the disc space anterior to the spinal cord.

The motion disc component of the present invention can be any prosthetic capable of restoring the natural motions of the intervertebral disc. In preferred embodiments, the motion disc is selected from the group consisting of an articulating disc, a cushion disc and a spring-based disc.

Preferred articulating motion devices are disclosed in U.S. Pat. Nos. 5,556,431 and 5,674,296, the specifications of which are incorporated by reference.

In some embodiments, the general structure of the articulating motion disc comprises:

a) a first prosthetic vertebral endplate comprising:
  i) an outer surface adapted to mate with a first vertebral body,
  ii) an inner surface having a first articulation surface,
  iii) a body portion connecting the inner and outer surfaces,
b) a second prosthetic vertebral endplate comprising:
  i) an outer surface adapted to mate with a second vertebral body, and
  ii) an inner surface comprising a first articulation surface,
c) a core member comprising:
  i) a first articulation surface adapted for articulation with the first articulation surface of the first endplate, and
  ii) a second articulation surface adapted for articulation with the first articulation surface of the second endplate,
wherein the core member is oriented to produce a first articulation interface between the first articulation surface of the first endplate and the first articulation surface of the core member, and a second articulation interface between the first articulation surface of the second endplate and the second articulation surface of the core member.

In some embodiments, the general structure of the articulating motion disc is a two piece design and comprises:

a) a first prosthetic vertebral endplate comprising:
  i) an outer surface adapted to mate with a first vertebral body,
  ii) an inner surface having a first articulation surface,
  iii) a body portion connecting the inner and outer surfaces,
b) a second prosthetic vertebral endplate comprising:
  i) an outer surface adapted to mate with a second vertebral body, and
  ii) an inner surface comprising a second articulation surface,
wherein the first and second articulation surfaces are oriented produce an articulation interface.

Preferably, the articulation interfaces form partial spheres.

The motion discs of the present invention can be adapted for use any of the lumbar, thoracic or cervical spine regions. In some embodiments wherein the motion disc is adapted for use in the lumbar region, the three-piece design having a core is selected. In some embodiments wherein the motion disc is adapted for use in the cervical region, the two-piece design is selected.

In some embodiments, the motion disc is implanted from the posterior side of the spine. In some embodiments, the motion disc is a ball and socket-based disc. In some embodiments, the motion disc takes the form of the motion disc disclosed in U.S. Ser. No. 11/351,710, filed Feb. 10, 2006, entitled "Intervertebral Disc Prosthesis Having Multiple Bearing Surfaces" (First Inventor Name) Kwak et al., the specification of which is hereby incorporated by reference in its entirety.

The ball and socket designs disclosed therein are generally capable of withstanding the physiologic axial loads impressed onto a disc, is unconstrained in both flexion and extension, has a controlled axial rotation and lateral bending, and has an anterior-posterior pure shear stop. It is typically adapted for posterior insertion into the anterior disc space, and allows for easy alignment.

When used to augment the ball and socket design in spinal support, the PDS device of the present invention allows for a large flexion/extension range of motion; has controlled stops for both flexion and extension, is pedicle-screw based, and supports AP shear through its ligament tension.

In some embodiments, particularly for use in the L5-S1 lumbrosacral area, the pedicle screws are situated sufficiently close to each other so as to obviate the need for the spacer. Therefore, in some embodiments, the spacer component of the device is eliminated. In this case, the inner portions of the opposing belt retainers oppose each other in the neutral zone and contact each other during spinal extension, thus acting as an extension stop as the spacer did in the first embodiment.

Figure 5B:
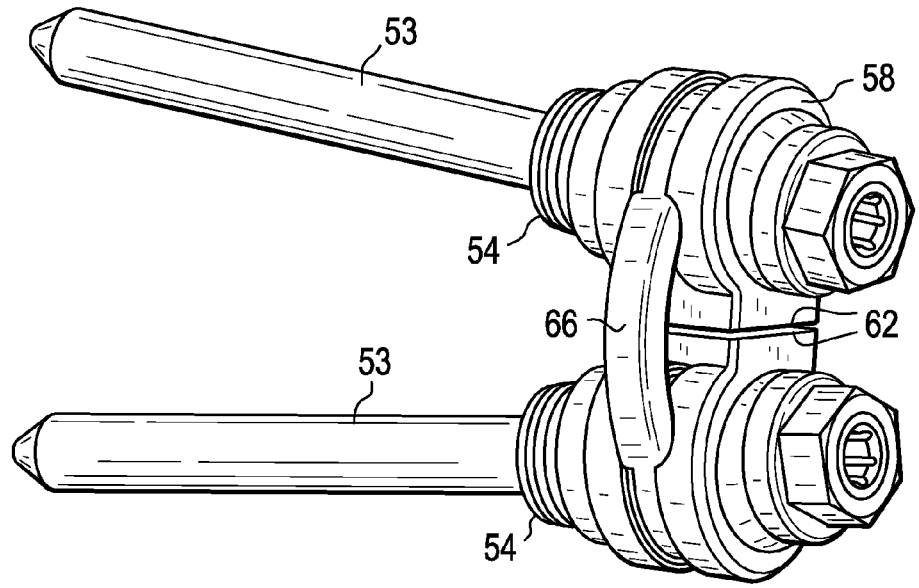
FIGS. 5*b*-5*c* disclose perspective views of the spacerless device of the present invention in extension and flexion.
Figure 5C:
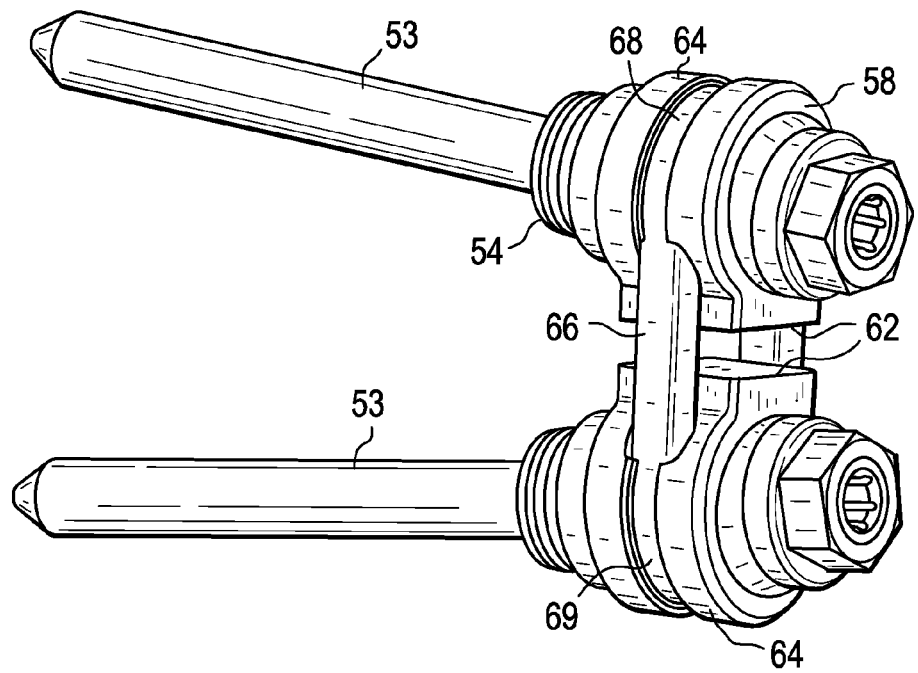

Now referring to FIG. 5a-c, and in accordance with the present invention, there is provided a spacerless posterior dynamic stabilization system, comprising:

a) first 51 and second 52 bone anchors having a distal end 53 having a threadform 54 and a proximal end 55,
b) first and second belt retainers 56, each retainer comprising an annulus 58 having a circumferential channel 60 therein, an inner portion 62 and an outer portion 64, the annulus fitting over the proximal end of the respective bone anchor, and
c) a first flexible belt ligament 66 having a first end portion 68 and a second end portion 69,
wherein each end portion of the flexible belt ligament is attached to a respective belt retainer (and preferably resides in the circumferential channel), and
wherein the inner portions of the belt retainers contact each other during spinal extension.

In preferred embodiments, each of the inner portions of the belt retainers are flat.

FIG. 5a provides an exploded perspective view of the spacerless device of the present invention.

Now referring to FIG. 5b, there is provided a perspective view of the spacerless device of the present invention, positioned as implanted in a functional spinal unit that is subject to spinal extension. During spinal extension, the two bone anchors move closer together as do the two belt retainers 56, thereby imparting a compressive force on the device. In this condition, the belt retainers act as the ultimate limiting feature of the spinal extension, as the inner portions 62 of the respective belt retainers come into contact. The belt ligament 68 is in a lax condition.

Now referring to FIG. 5c, there is provided perspective view of the spacerless device of the present invention, positioned as implanted in a functional spinal unit that is subject to spinal flexion. During spinal flexion, the two bone anchors move farther apart (as do the two belt retainers 5), thereby imparting a tensile force on the ligament 68. In this condition, the belt ligament acts as the ultimate limiting feature of the spinal flexion, as it is stretched to its ultimate length. The belt ligament is in a taut condition. Also in this condition, there is no contact between the belt retainers.

As above, the bone anchor and belt retainer combination of FIGS. 5a-5c may be considered to form a polyaxial screw. Thus, when it is stated that the bone anchors contact each other, such contact may include either direct contact, or indirect contact through a belt retainer. Therefore, in accordance with the present invention, there is provided a posterior dynamic stabilization system, comprising:

a) first and second bone anchors having a distal end having a threadform and a proximal end,
b) a first flexible belt ligament having a first end portion and a second end portion, and
wherein each end portion of the flexible belt ligament is attached to a respective bone anchor, and
wherein the first bone anchor contacts the second bone anchor during spinal extension.

I claim:

1. A posterior dynamic stabilization system, comprising:
   a) first and second bone anchors having a distal end having a first threadform and a proximal end,
   b) a single continuous belt having a first portion and a second portion, and
   c) a spacer having a first end and a second end, the spacer being disposed between the respective bone anchors,
   d) first and second belt retainers, each retainer comprising an annulus having a circumferential channel therein, the annulus fitting over the proximal end of the respective bone anchor,
   e) first and second side springs, wherein the first side spring wraps around the first portion of the belt, and the second side spring wraps around the second portion of the belt,
wherein the spacer is positioned between the two bone anchors to contact each bone anchor during spinal extension,
wherein each belt retainer is locked onto a respective bone anchor,
wherein each circumferential channel has an inner portion and an outer portion,
wherein the belt is disposed within an outer portion of each channel, and
wherein the spacer is disposed within the belt.

2. The system of claim 1, wherein the proximal end of the bone anchors having a second threadform, and further comprising f) first and second threaded locking nuts mating with the second threadforms.

3. The system of claim 2 wherein the spacer has a longitudinal length that is slightly less than a distance between the locking nuts.

4. The system of claim 1 wherein the first end of the spacer contacts the first belt retainer and the second end of the spacer contacts the second belt retainer during spinal extension.

5. The system of claim 1 wherein each end of the spacer has a shape corresponding to a shape of the belt retainer it contacts.

6. The system of claim 1 wherein each end of the spacer has a concave shape corresponding to a convex shape of the belt retainer it contacts.

7. The system of claim 1 wherein each end of the spacer has a concave portion of a circle corresponding to a convex circular shape of the belt retainer it contacts.

8. The system of claim 1 wherein the spacer comprises two side surfaces defining a transverse width that is slightly less than a diameter of the belt retainers.

9. The system of claim 8 wherein the two side surfaces of the spacer are parallel to each other and flat.

10. The system of claim 8 wherein each of the two side surfaces of the spacer has a concave recesses therein.

11. The system of claim 8 wherein each of the two side surfaces of the spacer has a pair of concave recesses therein.

12. A kit for use in spinal stabilization, comprising:
   i) a posterior dynamic stabilization system, comprising:
      a) first and second bone anchors having a distal end having a first threadform and a proximal end,
      b) a single continuous belt having a first portion and a second portion, and
      c) a spacer having a first end and a second end, the spacer being disposed between the respective bone anchors,
      d) first and second belt retainers, each retainer comprising an annulus having a circumferential channel therein, the annulus fitting over the proximal end of the respective bone anchor,
      e) first and second side springs, wherein the first side spring wraps around the first portion of the belt, and the second side spring wraps around the second portion of the belt,
   wherein the spacer is positioned between the two bone anchors to contact each bone anchor during spinal extension,
   wherein each belt retainer is locked onto a respective bone anchor,
   wherein each circumferential channel has an inner portion and an outer portion,
   wherein the belt is disposed within an outer portion of each channel, and
   wherein the spacer is disposed within the belt,
   and
      ii) an intervertebral disc replacement.

13. A method of stabilizing the spine comprising the steps of:
   i) implanting a posterior dynamic stabilization system on a posterior side of a spinal column, the system comprising:
      a) first and second bone anchors having a distal end having a first threadform and a proximal end having a second threadform,
      b) a single continuous belt having a first portion and a second portion, and
      c) a spacer having a first end and a second end, the spacer being disposed between the respective bone anchors,
      d) first and second belt retainers, each retainer comprising an annulus having a circumferential channel therein, the annulus fitting over the proximal end of the respective bone anchor,
      e) first and second side springs, wherein the first side spring wraps around the first portion of the belt, and the second side spring wraps around the second portion of the belt,
   wherein the spacer is positioned between the two bone anchors to contact each bone anchor during spinal extension,
   wherein each belt retainer is locked onto a respective bone anchor,
   wherein each circumferential channel has an inner portion and an outer portion,
   wherein the belt is disposed within an outer portion of each channel, and
   wherein the spacer is disposed within the belt,
   and
      ii) implanting an intervertebral disc replacement on an anterior side of the spinal column.

14. A posterior dynamic stabilization system, comprising:
   a) first and second bone anchors having a distal end having a first threadform and a proximal end,
   b) first and second belt retainers, each retainer comprising an annulus having a circumferential channel therein, an inner portion and an outer portion, the annulus fitting over the proximal end of the respective bone anchor, and
   c) a single continuous belt having a first portion and a second portion,
   d) first and second side springs, wherein the first side spring wraps around the first portion of the belt, and the second side spring wraps around the second portion of the belt,
wherein the inner portions of the belt retainers contact each other during spinal extension,
wherein each belt retainer is locked onto a respective bone anchor,
wherein each circumferential channel has an inner portion and an outer portion,
wherein the belt is disposed within an outer portion of each channel, and
wherein the spacer is disposed within the belt.

15. The system of claim 14 wherein each portion of the belt resides in the respective circumferential channel.

* * * * *